United States Patent [19]
Shultz et al.

[11] Patent Number: 6,103,647
[45] Date of Patent: Aug. 15, 2000

[54] NONWOVEN FABRIC LAMINATE WITH GOOD CONFORMABILITY

[75] Inventors: Jay Sheldon Shultz; Susan Elaine Shawver; Leslie Warren Collier, IV, all of Roswell; Paul Windsor Estey, Cumming, all of Ga.

[73] Assignee: Kimberly-Clark Worldwide, Inc., Neenah, Wis.

[21] Appl. No.: 08/615,378

[22] Filed: Mar. 14, 1996

[51] Int. Cl.[7] .......................... A41D 31/00; A41D 13/12; A61B 19/08; B32B 33/00
[52] U.S. Cl. .......................... 442/346; 128/849; 442/392; 604/385.2
[58] Field of Search .................................. 442/392, 346; 604/385.2; 128/849

[56] References Cited

U.S. PATENT DOCUMENTS

| | | | |
|---|---|---|---|
| 3,338,992 | 8/1967 | Kinney | 264/24 |
| 3,341,394 | 9/1967 | Kinney | 161/72 |
| 3,502,538 | 3/1970 | Petersen | 161/150 |
| 3,502,763 | 3/1970 | Hartmann | 264/210 |
| 3,542,615 | 11/1970 | Dobo et al. | 156/181 |
| 3,692,618 | 9/1972 | Dorschner et al. | 161/72 |
| 3,802,817 | 4/1974 | Matsuki et al. | 425/66 |
| 3,849,241 | 11/1974 | Butin | 161/169 |
| 3,855,046 | 12/1974 | Hansen et al. | 161/150 |
| 4,041,203 | 8/1977 | Brock et al. | 428/157 |
| 4,340,563 | 7/1982 | Appel et al. | 264/518 |
| 4,374,888 | 2/1983 | Bornslaeger | 428/198 |
| 4,542,199 | 9/1985 | Kaminsky et al. | 526/160 |
| 4,652,487 | 3/1987 | Morman | 428/138 |
| 4,655,760 | 4/1987 | Morman et al. | 604/385.1 |
| 4,657,802 | 4/1987 | Morman | 428/152 |
| 4,663,220 | 5/1987 | Wisneski et al. | 428/221 |
| 4,692,368 | 9/1987 | Taylor et al. | 428/137 |
| 4,692,371 | 9/1987 | Morman et al. | 428/224 |
| 4,704,116 | 11/1987 | Enloe | 604/385 |
| 4,707,398 | 11/1987 | Boggs | 428/224 |
| 4,710,187 | 12/1987 | Boland et al. | 604/385 |
| 4,720,415 | 1/1988 | Vander Wielen et al. | 428/152 |
| 4,724,184 | 2/1988 | Killian et al. | 428/227 |
| 4,741,949 | 5/1988 | Morman et al. | 428/224 |
| 4,781,966 | 11/1988 | Taylor | 428/152 |
| 4,789,699 | 12/1988 | Kieffer et al. | 524/271 |
| 4,803,117 | 2/1989 | Daponte | 428/228 |
| 4,820,572 | 4/1989 | Killian et al. | 428/227 |
| 4,822,435 | 4/1989 | Igaue et al. | 156/164 |
| 4,923,742 | 5/1990 | Killian et al. | 428/283 |
| 4,965,122 | 10/1990 | Morman | 428/225 |
| 4,981,747 | 1/1991 | Morman | 428/198 |
| 5,026,364 | 6/1991 | Robertson | 604/385.1 |
| 5,064,802 | 11/1991 | Stevens et al. | 502/155 |
| 5,108,820 | 4/1992 | Kaneko et al. | 428/198 |
| 5,169,706 | 12/1992 | Collier | 428/152 |
| 5,189,192 | 2/1993 | LaPointe et al. | 556/11 |
| 5,204,429 | 4/1993 | Karninsky et al. | 526/308 |
| 5,226,992 | 7/1993 | Morman | 156/62.4 |
| 5,272,236 | 12/1993 | Lai et al. | 526/348.5 |
| 5,278,272 | 1/1994 | Lai et al. | 526/348.5 |
| 5,302,454 | 4/1994 | Cecchin | 428/402 |
| 5,304,599 | 4/1994 | Himes | 525/98 |
| 5,332,613 | 7/1994 | Taylor et al. | 428/152 |
| 5,336,545 | 8/1994 | Morman | 428/152 |
| 5,336,552 | 8/1994 | Strack et al. | 428/224 |
| 5,349,100 | 9/1994 | Mintz | 585/350 |
| 5,352,749 | 10/1994 | DeChellis et al. | 526/68 |
| 5,368,927 | 11/1994 | Lesea et al. | 428/288 |
| 5,374,696 | 12/1994 | Rosen et al. | 526/126 |
| 5,376,198 | 12/1994 | Fahrenkrug et al. | 156/164 |
| 5,382,400 | 1/1995 | Pike et al. | 264/168 |
| 5,413,570 | 5/1995 | Enloe | 604/385.2 |
| 5,413,811 | 5/1995 | Fitting et al. | 427/176 |
| 5,415,644 | 5/1995 | Enloe | 604/385.2 |

FOREIGN PATENT DOCUMENTS

| | | |
|---|---|---|
| 0400333 A2 | 12/1990 | European Pat. Off. . |
| 0 416 620 | 3/1991 | European Pat. Off. .......... B32B 5/26 |
| 0444671 A3 | 9/1991 | European Pat. Off. . |
| 0472946 A2 | 3/1992 | European Pat. Off. . |
| 0 586 937 | 3/1994 | European Pat. Off. ....... D04H 13/00 |
| 0602 613A1 | 6/1994 | European Pat. Off. . |
| 0 674 035 | 9/1995 | European Pat. Off. ......... D04H 1/56 |
| 0 712 892 | 5/1996 | European Pat. Off. ........ C08L 23/16 |
| 94/28224 | 12/1994 | WIPO .......................... D04H 13/00 |

OTHER PUBLICATIONS

Bodford, A.C., Multidenier NW Fabrics, For Leg Cuff and Other Diaper Applications, Nonwovens World—Summer 1995, pp. 59–62.

Wagener K.B., Oscillating Catalysts: A New Twist for Plastics, Science vol. 267, p. 191, Jan. 1995.

Coates G.W. et al., Oscillating Stereocontrol: A Strategy for the Synthesis of Thermoplastic Elastomeric Polypropylene, Science, vol. 267, pp. 267–219, Jan. 13, 1995.

Manson, J.A. et al., Polymer Blends and Composites, Bicomponent and Biconstituent Fibers, Sec 9.2, pp. 273–277.

Primary Examiner—James C. Cannon
Attorney, Agent, or Firm—James B. Robinson; William D. Herrick

[57] ABSTRACT

There is provided a laminate having at least one layer of meltblown elastic fibers bonded on either side with a layer of soft non-elastic fibers of greater than 7 microns in average diameter. The laminate has a drape stiffness less than half of a similar fabric having a layer of meltblown non-elastic fibers in place of the layer of meltblown elastic fibers.

24 Claims, No Drawings

NONWOVEN FABRIC LAMINATE WITH GOOD CONFORMABILITY

BACKGROUND OF THE INVENTION

This invention relates to nonwoven fabrics for use in garments, personal care products and infection control products.

In the case of items to be worn like, for example, gowns, the softness, drape and conformability are important considerations. Softness, at least for the side against the wearer, is an important consideration to avoid skin irritaton. Softness becomes more of an issue for longer term usage such as in the case of a surgical gown which may be worn for a period of hours. Conformability is the degree to which a fabric will adapt itself to the shape of an object it is covering. A highly conformable fabric, for example will adapt itself well to a wearer's body and as a result will not feel stiff. A stiff fabric is, of course, to be avoided when designing a comfortable garment. One measure of the conformability of a fabric is the drape stiffness.

A fabric for these application must also have the ability to stretch and recover from such stretching or deformation and must also be breathable so as not to inhibit skin comfort.

It is an object of this invention to provide a nonwoven fabric which may be used in garments and infection control products and which is breathable while having good softness, drape and conformability.

SUMMARY OF THE INVENTION

The objects of the invention are satisfied by a laminate of having at least one layer of meltblown elastic fibers bonded on either side with a layer of soft non-elastic fibers of greater than 7 microns in average diameter. The fabric so produced has a drape stiffness less than half of a similar fabric having a layer of meltblown non-elastic fibers in place of the layer of meltblown elastic fibers. The soft fibers may be made from polyethylene and polypropylene and may be conjugate side-by-side, sheath core, islands in the sea or other configurations.

DEFINITIONS

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

As used herein, the term "elastic" when referring to a fiber or fabric mean a material which upon application of a biasing force, is stretchable to a stretched, biased length which is at least about 150 percent, or one and a half times, its relaxed, unstretched length, and which will recover at least 50 percent of its elongation upon release of the stretching, biasing force. Elastic materials are also referred to as "elastomeric" and sometimes as "plastomeric". Non-elastic materials are those which do not meet the definition of "elastic".

As used herein the term "recover" refers to a contraction of a stretched material upon termination of a biasing force following stretching of the material by application of the biasing force. For example, if a material having a relaxed, unbiased length of one (1) inch was elongated 50 percent by stretching to a length of one and one half (1.5) inches the material would have a stretched length that is 150 percent of its relaxed length. If this exemplary stretched material contracted or recovered to a length of one and one tenth (1.1) inches after release of the biasing and stretching force, the material would have recovered 80 percent (0.4 inch) of its elongation.

Conventionally, "stretch bonded" refers to an elastic member being bonded to another member while the elastic member is extended. "Stretch bonded laminate" or SBL conventionally refers to a composite material having at least two layers in which one layer is a gatherable layer and the other layer is an elastic layer. The layers are joined together when the elastic layer is in an extended condition so that upon relaxing the layers, the gatherable layer is gathered. Such a multilayer composite elastic material may be stretched to the extent that the nonelastic material gathered between the bond locations allows the elastic material to elongate. One type of multilayer composite elastic material is disclosed, for example, by U.S. Pat. No. 4,720,415 to Vander Wielen et al., which is hereby incorporated by reference in its entirety, and in which multiple layers of the same polymer produced from multiple banks of extruders are used. Other composite elastic materials are disclosed in U.S. Pat. No. 4,789,699 to Kieffer et al., U.S. Pat. No. 4,781,966 to Taylor and U.S. Pat. Nos. 4,657,802 and 4,652,487 to Morman and U.S. Pat. Nos. 4,655,760 and 4,692,371 to Morman et al.

Conventionally, "neck bonded" refers to an elastic member being bonded to a non-elastic member while the non-elastic member is extended or necked. "Neck bonded laminate" or NBL conventionally refers to a composite material having at least two layers in which one layer is a necked, non-elastic layer and the other layer is an elastic layer. The layers are joined together when the non-elastic layer is in an extended condition. Examples of neck-bonded laminates are such as those described in U.S. Pat. Nos. 5,226,992, 4,981, 747, 4,965,122 and 5,336,545 to Morman.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No.

3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Levy, and U.S. Pat. No. 3,542,615 to Dobo et al. Spunbond fibers are generally not tacky when they are deposited onto a collecting surface. Spunbond fibers are microfibers which are generally continuous and have average diameters (from a sample size of at least 10) larger than 7 microns, more particularly, between about 10 and 30 microns.

As used herein the term "meltblown fibers" means fibers formed by extruding a molten thermoplastic material through a plurality of fine, usually circular, die capillaries as molten threads or filaments into converging high velocity gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Buntin. Meltblown fibers are microfibers which may be continuous or discontinuous, are usually smaller than 10 microns in average diameter, and are generally tacky when deposited onto a collecting surface.

Spunbond and meltblown fabrics may be combined into "SMS laminates" wherein some of the layers are spunbond and some meltblown such as a spunbond/meltblown/spunbond (SMS) laminate as disclosed in U.S. Pat. No. 4,041,203 to Brock et al., U.S. Pat. No. 5,169,706 to Collier, et al, and U.S. Pat. No. 4,374,888 to Bomslaeger. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (6 to 400 gsm), or more particularly from about 0.75 to about 3 osy.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configuration of the material. These configurations include, but are not limited to isotactic, syndiotactic and random symmetries.

As used herein the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios.

As used herein "thermal point bonding" involves passing a fabric or web of fibers to be bonded between a heated calender roll and an anvil roll. The calender roll is usually, though not always, patterned in some way so that the entire fabric is not bonded across its entire surface. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen and Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds and a wire weave pattern looking as the name suggests, e.g. like a window screen. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

As used herein, through-air bonding or "TAB" means a process of bonding a nonwoven bicomponent fiber web in which air which is sufficiently hot to melt one of the polymers of which the fibers of the web are made is forced through the web. The air velocity is between 100 and 500 feet per minute and the dwell time may be as long as 6 seconds. The melting and resolidification of the polymer provides the bonding. Through air bonding has relatively restricted variability and since through-air bonding TAB requires the melting of at least one component to accomplish bonding, it is restricted to webs with two components like conjugate fibers or those which include an adhesive. In the through-air bonder, air having a temperature above the melting temperature of one component and below the melting temperature of another component is directed from a surrounding hood, through the web, and into a perforated roller supporting the web. Alternatively, the through-air bonder may be a flat arrangement wherein the air is directed vertically downward onto the web. The operating conditions of the two configurations are similar, the primary difference being the geometry of the web during bonding. The hot air melts the lower melting polymer component and thereby forms bonds between the filaments to integrate the web.

As used herein, the term "personal care product" means diapers, training pants, absorbent underpants, adult incontinence products, and feminine hygiene products. Such products generally include outer cover layers and inner absorbent layers.

As used herein, the term "garment" means any type of non-medically oriented apparel which may be worn. This includes industrial work wear and coveralls, undergarments, pants, shirts, jackets, gloves, socks, and the like.

As used herein, the term "infection control product" means medically oriented items such as surgical gowns and drapes, face masks, head coverings like bouffant caps, surgical caps and hoods, footwear like shoe coverings, boot covers and slippers, wound dressings, bandages, sterilization wraps, wipers, garments like lab coats, coveralls, aprons and jackets, patient bedding, stretcher and bassinet sheets, and the like.

TEST METHODS

Hydrohead: A measure of the liquid barrier properties of a fabric is the hydrohead test. The hydrohead test determines the pressure of water (in mbar) which the fabric will support before a predetermined amount of liquid passes through. A fabric with a higher hydrohead reading indicates it has a greater barrier to liquid penetration than a fabric with a lower hydrohead. The hydrohead test is performed according to Federal Test Standard No. 191A, Method 5514.

Drape: The drape stiffness test, also sometimes called the cantilever bending test, determines the bending length of a fabric using the principle of cantilever bending of the fabric under its own weight. The bending length is a measure of the interaction between fabric weight and fabric stiffness. A 1 inch (2.54 cm) by 8 inch (20.3 cm) fabric strip is slid, at 4.75 inches per minute (12 cm/min) in a direction parallel to its long dimension so that its leading edge projects from the edge of a horizontal surface. The length of the overhang is measured when the tip of the specimen is depressed under its own weight to the point where the line joining the tip of the fabric to the edge of the platform makes a 41.5 degree angle with the horizontal. The longer the overhang the slower the specimen was to bend, indicating a stiffer fabric. The drape stiffness is calculated as 0.5 x bending length. A total of 5 samples of each fabric should be taken. This procedure conforms to ASTM standard test D-1388 except for the fabric length which is different (longer). The test equipment used is a Cantilever Bending tester model 79-10 available from Testing Machines Inc., 400 Bayview Ave., Amityville, N.Y. 11701. As in most testing, the sample should be conditioned to ASTM conditions of 65±2 percent relative humidity and 72±2° F. (22±1° C.), or TAPPI conditions of 50±2 percent relative humidity and 72±1.8° F. prior to testing.

Mullen Burst: This test measures the resistance of textile fabrics to bursting when subjected to hydraulic pressure. The bursting strength is defined as the hydrostatic pressure required to rupture a fabric by distending it with a force, applied through a rubber diaphragm, at right angles to the plane of the fabric. This method measures the bursting strength of products up to 0.6 mm thick, having a bursting strength up to about 200 pounds per square inch. The pressure is generated by forcing a liquid (glycerin) into a chamber at the rate of 95±5 ml/min. The specimen, held between annular claims, is subjected to increasing pressure at a controlled rate until the specimen ruptures. The bursting strength is expressed in pounds. This procedure conforms to TAPPI official standard T-403 os-76, except that specimen size is 5 inches (12.6 cm) square and ten specimens are tested. The test equipment used is a motor driven Mullen bursting strength tester from B.G. Perkins & Son Inc., G.P.O. 366, Chicopee, Mass. 01021 or from Testing Machines Inc., 400 Bayview Ave., Amityville, N.Y. 11701. The sample should be conditioned to ASTM conditions of 65±2 percent relative humidity and 72±2° F. (22±1° C.), or TAPPI conditions of 50±2 percent relative humidity and 72±1.8° F. prior to testing.

Cup Crush: The softness of a nonwoven fabric may be measured according to the "cup crush" test. The cup crush test evaluates fabric stiffness by measuring the peak load (also called the "cup crush load" or just "cup crush") required for a 4.5 cm diameter hemispherically shaped foot to crush a 23 cm by 23 cm piece of fabric shaped into an approximately 6.5 cm diameter by 6.5 cm tall inverted cup while the cup shaped fabric is surrounded by an approximately 6.5 cm diameter cylinder to maintain a uniform deformation of the cup shaped fabric. An average of 10 readings is used. The foot and the cup are aligned to avoid contact between the cup walls and the foot which could affect the readings. The peak load is measured while the foot is descending at a rate of about 0.25 inches per second (380 mm per minute) and is measured in grams. The cup crush test also yields a value for the total energy required to crush a sample (the "cup crush energy") which is the energy from the start of the test to the peak load point, i.e. the area under the curve formed by the load in grams on one axis and the distance the foot travels in millimeters on the other. Cup crush energy is therefore reported in gm-mm. Lower cup crush values indicate a softer laminate. A suitable device for measuring cup crush is a model FTD-G-500 load cell (500 gram range) available from the Schaevitz Company, Pennsauken, N.J.

DETAILED DESCRIPTION OF THE INVENTION

Thermoplastic polymers are useful in the production of films, fibers and webs for use in a variety of products such as personal care products, infection control products, garments and protective covers.

Materials for gowns must have good strength, durability and puncture resistance. It is also usually desired that such materials be thin in order to retain minimal heat and preferably to conform to an object easily for increased comfort. Increased softness, conformability and comfort have been pursued in the past by topical treatments and/or mechanical means, such as that discussed in U.S. Pat. No. 5,413,811 to Fitting et al. which uses chemical and mechanical means to increase softness. Also discussed in Fitting is the wash softening process and other softening processes.

The inventors have found that a laminate of spunbond and meltblown fabrics having lower drape stiffness values, and therefore greater conformability and comfort, surprisingly may be produced by using elastic meltblown fabric in the interior. While one would expect the substitution of an elastic interior meltblown layer for an inelastic interior meltblown layer to have little effect on external fabric sensory characteristics, such is not the case. Even though the overall fabric is not elastic, the interior elastic meltblown layer produces a dramatic decrease in drape stiffness. This appears to be irrespective of the type of elastic meltblown employed.

The barrier properties of a fabric may be measured using the hydrohead test. This test determines the height of water (in millibars) which the fabric will support before a predetermined amount of liquid passes through. A fabric with a higher hydrohead reading indicates it has a greater barrier to liquid penetration than a fabric with a lower hydrohead. The hydrohead value of a material will be influenced by such factors as the size of the fibers, finer fibers producing smaller pores for liquid to pass through, and the hydrophobicity of the fibers. The inventors believe that a material having a hydrohead value of at least 10 millibars is necessary in infection control applications.

The strength of a fabric may be measured by the Mullen Burst strength test.

The conformability of a fabric may be measured by the Drape Stiffness test, or simply Drape test. This test measures how far a fabric may be extended off the edge of a table before bending. The lower the reading the more conformable, and presumably comfortable, a fabric will be on the wearer.

Elastomeric thermoplastic polymers useful in the practice of this invention may be those made from block copolymers such as polyurethanes, copolyesters, polyamide polyether block copolymers, ethylene vinyl acetates (EVA), block copolymers having the general formula A-B-A' or A-B like copoly(styrenelethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene) and the like.

Useful elastomeric resins include block copolymers having the general formula A-B-A' or A-B, where A and A' are each a thermoplastic polymer endblock which contains a styrenic moiety such as a poly (vinyl arene) and where B is an elastomeric polymer midblock such as a conjugated diene or a lower alkene polymer. Block copolymers of the A-B-A' type can have different or the same thermoplastic block polymers for the A and A' blocks, and the present block copolymers are intended to embrace linear, branched and radial block copolymers. In this regard, the radial block copolymers may be designated $(A-B)_m-X$, wherein X is a polyfunctional atom or molecule and in which each $(A-B)_m$-radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer", and particularly "A-B-A'" and "A-B" block copolymer, is intended to embrace all block copolymers having such rubbery blocks and thermoplastic blocks as discussed above, which can be extruded (e.g., by meltblowing), and without limitation as to the number of blocks. The elastomeric nonwoven web may be formed from, for example, elastomeric (polystyrene/poly(ethylene-butylene)/polystyrene) block copolymers. Commercial examples of such elastomeric copolymers are, for example, those sold as part of the polymer family known as KRATON® materials which are available from Shell Chemical Company of Houston, Tex. KRATON® block copolymers are available in several different formulations, a number of which are identified in U.S. Pat. Nos. 4,663,220 and 5,304,599, hereby incorporated by reference.

Polymers composed of an elastomeric A-B-A-B tetrablock copolymer may also be used in the practice of this invention. Such polymers are discussed in U.S. Pat. No. 5,332,613 to Taylor et al. In such polymers, A is a thermoplastic polymer block and B is an isoprene monomer unit hydrogenated to substantially a poly(ethylene-propylene) monomer unit. An example of such a tetrablock copolymer is a styrene-poly(ethylene-propylene)-styrene-poly(ethylene-propylene) or SEPSEP elastomeric block copolymer available from the Shell Chemical Company of Houston, Tex. as part of the KRATON® polymer family.

Other exemplary elastomeric materials which may be used include polyurethane elastomeric materials such as, for example, those available under the trademark ESTANE® from B. F. Goodrich & Co. or MORTHANE® from Morton Thiokol Corp., polyester elastomeric materials such as, for example, those available under the trade designation HYTREL® from E. I. DuPont De Nemours & Company, and those known as ARNITEL®, formerly available from Akzo Plastics of Arnhem, Holland and now available from DSM of Sittard, Holland.

Another suitable material is a polyester block amide copolymer having the formula:

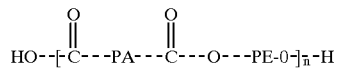

where n is a positive integer, PA represents a polyamide polymer segment and PE represents a polyether polymer segment. In particular, the polyether block amide copolymer has a melting point of from about 150° C. to about 170° C., as measured in accordance with ASTM D789; a melt index of from about 6 grams per 10 minutes to about 25 grams per 10 minutes, as measured in accordance with ASTM D-1238, condition Q (235 C/1 Kg load); a modulus of elasticity in flexure of from about 20 Mpa to about 200 Mpa, as measured in accordance with ASTM D-790; a tensile strength at break of from about 29 Mpa to about 33 Mpa as measured in accordance with ASTM D-638 and an ultimate elongation at break of from about 500 percent to about 700 percent as measured by ASTM D-638. A particular embodiment of the polyether block amide copolymer has a melting point of about 152° C. as measured in accordance with ASTM D-789; a melt index of about 7 grams per 10 minutes, as measured in accordance with ASTM D-1238, condition Q (235 C/1 Kg load); a modulus of elasticity in flexure of about 29.50 Mpa, as measured in accordance with ASTM D-790; a tensile strength at break of about 29 Mpa, a measured in accordance with ASTM D-639; and an elongation at break of about 650 percent as measured in accordance with ASTM D-638. Such materials are available in various grades under the trade designation PEBAX® from Atochem Inc. Polymers Division (RILSAN®), of Glen Rock, N.J. Examples of the use of such polymers may be found in U.S. Pat. Nos. 4,724,184, 4,820,572 and 4,923,742 hereby incorporated by reference, to Killian et al. and assigned to the same assignee as this invention.

Elastomeric polymers also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117.

The thermoplastic copolyester elastomers include copolyetheresters having the general formula:

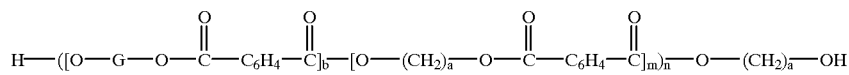

where "G" is selected from the group consisting of poly (oxyethylene)-alpha,omega-diol, poly(oxypropylene)-alpha, omega-diol, poly(oxytetramethylene)-alpha,omega-diol and "a" and "b" are positive integers including 2, 4 and 6, "m" and "n" are positive integers including 1–20. Such materials generally have an elongation at break of from about 600 percent to 750 percent when measured in accordance with ASTM D-638 and a melt point of from about 350° F. to about 400° F. (176 to 205° C.) when measured in accordance with ASTM D-2117.

Commercial examples of such copolyester materials are, for example, those known as ARNITEL®, formerly available from Akzo Plastics of Amhem, Holland and now available from DSM of Sittard, Holland, or those known as HYTREL® which are available from E.I. duPont de Nemours of Wilmington, Del. Formation of an elastomeric nonwoven web from polyester elastomeric materials is disclosed in, for example, U.S. Pat. No. 4,741,949 to Morman et al. and U.S. Pat. No. 4,707,398 to Boggs, hereby incorporated by reference.

The above mentioned polymers are generally limited to meltblowing applications though the inventors have had some success in spunbonding some of them. The inventors contemplate, therefore, that these materials may be used for either spunbonding or meltblowing.

These materials have recently been joined by a new class of polymers which, when made into fabric, has excellent barrier, breathability, elasticity and a pleasing hand. The new class of polymers is referred to as "metallocene" polymers or as produced according to the metallocene process. Metallocene polymers have been developed which may be processed by meltblowing or spunbonding.

The metallocene process generally uses a metallocene catalyst which is activated, i.e. ionized, by a co-catalyst. Metallocene catalysts include bis(n-butylcyclopentadienyl) titanium dichloride, bis(n-butylcyclopentadienyl)zirconium dichloride, bis(cyclopentadienyl)scandium chloride, bis (indenyl)zirconium dichloride, bis(methylcyclopentadienyl) titanium dichloride, bis(methylcyclopentadienyl)zirconium dichloride, cobaltocene, cyclopentadienyltitanium trichloride, ferrocene, hafnocene dichloride, isopropyl (cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow.

The metallocene process, and particularly the catalysts and catalyst support systems are the subject of a number of patents. U.S. Pat. No. 4,542,199 to Kaminsky et al. describes a procedure wherein methylaluminoxane (MAO) is added to toluene, the metallocene catalyst of the general formula (cyclopentadienyl)2MeRHal wherein Me is a transition metal, Hal is a halogen and R is cyclopentadienyl or a C1 to C6 alkyl radical or a halogen, is added, and ethylene is then added to form polyethylene. U.S. Pat. No. 5,189,192 to LaPointe et al. and assigned to Dow Chemical describes a process for preparing addition polymerization catalysts via metal center oxidation. U.S. Pat. No. 5,352,749 to Exxon Chemical Patents, Inc. describes a method for polymerizing monomers in fluidized beds. U.S. Pat. No. 5,349,100 describes chiral metallocene compounds and preparation thereof by creation of a chiral center by enantioselective hydride transfer.

Co-catalysts are materials such as methylaluminoxane (MAO) which is the most common, other alkylaluminums and boron containing compounds like tris (pentafluorophenyl)boron, lithium tetrakis (pentafluorophenyl)boron, and dimethylanilinium tetrakis (pentafluorophenyl)boron. Research is continuing on other co-catalyst systems or the possibility of minimizing or even eliminating the alkylaluminums because of handling and product contamination issues. The important point is that the metallocene catalyst be activated or ionized to a cationic form for reaction with the monomer(s) to be polymerized.

Polymers produced using metallocene catalysts have the unique advantage of having a very narrow molecular weight range. Polydispersity numbers (Mw/Mn) of below 4 and as even below 2 are possible for metallocene produced polymers. These polymers also have a narrow short chain branching distribution when compared to otherwise similar Ziegler-Natta produced type polymers.

It is also possible using a metallocene catalyst system to control the isotacticity of the polymer quite closely when stereo selective metallocene catalysts are employed. In fact, polymers have been produced having an isotacticity of in excess of 99 percent. It is also possible to produce highly syndiotactic polypropylene using this system.

Controlling the tacticity of a polymer can also result in the production of a polymer which contains blocks of isotactic and blocks of atactic material alternating over the length of the polymer chain. This construction results in an elastic polymer by virtue of the atactic portion. Such polymer synthesis is discussed in the journal *Science*, vol. 267, (Jan. 13, 1995) at p. 191 in an article by K. B. Wagner. Wagner, in discussing the work of Coates and Waymouth, explains that the catalyst oscillates between the stereochemical forms resulting in a polymer chain having running lengths of isotactic sterocenters connected to running lengths of atactic centers. Isotactic dominance is reduced producing elasticity. Geoffrey W. Coates and Robert M. Waymouth, in an article entitled "Oscillating Stereocontrol: A Strategy for the Synthesis of Thermoplastic Elastomeric Polypropylene" at page 217 in the same issue, discuss their work in which they used metallocene bis(2-phenylindenyl)-zirconium dichloride in the presence of methylaluminoxane (MAO), and, by varying the pressure and temperature in the reactor, oscillate the polymer form between isotactic and atactic.

Commercial production of metallocene polymers is somewhat limited but growing. Such polymers are available from Exxon Chemical Company of Baytown, Tex. under the trade name ACHIEVE® for polypropylene based polymers and EXACT® for polyethylene based polymers. A joint venture of the Dow Chemical Company of Midland, Mich. and E.I Dupont called Dupont Dow Elastomers L.L.C. has polymers commercially available under the name ENGAGE®. These materials are believed to be produced using non-stereo selective metallocene catalysts. Exxon generally refers to their metallocene catalyst technology as "single site" catalysts while Dow refers to theirs as "constrained geometry" catalysts under the name INSITE® to distinguish them from traditional Ziegler-Natta catalysts which have multiple reaction sites. Other manufacturers such as Fina Oil, BASF, Amoco, Hoechst and Mobil are active in this area and it is believed that the availability of polymers produced according to this technology will grow substantially in the next decade. In the practice of the instant invention, elastic polyolefins like polypropylene and polyethylene are preferred, most especially elastic polypropylene.

Regarding metallocene based elastomeric polymers, U.S. Pat. No. 5,204,429 to Kaminsky et al. describes a process which may produce elastic copolymers from cycloolefins and linear olefins using a catalyst which is a sterorigid chiral metallocene transition metal compound and an aluminoxane. The polymerization is carried out in an inert solvent such as an aliphatic or cycloaliphatic hydrocarbon such as toluene. The reaction may also occur in the gas phase using the monomers to be polymerized as the solvent. U.S. Pat. Nos. 5,278,272 and 5,272,236, both to Lai et al., assigned to Dow Chemical and entitled "Elastic Substantially Linear-Olefin Polymers" describe polymers having particular elastic properties.

Suitable polymers for the elastic layer are available commercially under the trade designation "Catalloy" from the Himont Chemical Company of Wilmington, Del., and polypropylene. Specific commercial examples are Catalloy KS-084P and Catalloy KS-057P. These types of polymers are disclosed in European Patent Application EP 0444671 A3 (based on Application number 91103014.6), European Patent Application EP 0472946 A2 (based on Application number 91112955.9), European Patent Application EP 0400333 A2 (based on Application number 90108051.5), U.S. Pat. No. 5,302,454 and U.S. Pat. No. 5,368,927.

European Patent Application EP 0444671 A3 teaches a composition comprising first, 10–60 weight percent of a homopolymer polypropylene having an isotactic index greater than 90 or or a crystalline copolymer of propylene with ethylene and/or other alpha-olefins containing more than 85 weight percent of propylene and having an isotactic index greater than 85; second, 10–40 weight percent of a copolymer containing prevailingly ethylene, which is insoluble in xylene at room temperature; and third, 30–60 weight percent of an amorphous ethylene-propylene copolymer, which is soluble in xylene at room temperature and contains 40–70 weight percent of ethylene, wherein the propylene polymer composition has a ratio between the intrinsic viscosities, in tetrahydronaphthalene at 135° C., of the portion soluble in xylene and of the portion insoluble in xylene at room temperature of from 0.8 to 1.2.

European Patent Application EP 0472946 A2 teaches a composition comprising first, 10–50 weight percent of a homopolymer polypropylene having an isotactic index greater than 80 or or a crystalline copolymer of propylene with ethylene, a $CH_2=CHR$ alpha-olefin where R is a 2–8 carbon alkyl radical or combinations thereof, which copolymer contains more than 85 weight percent of propylene; second, 5–20 weight percent of a copolymer containing ethylene, which is insoluble in xylene at room temperature; and third, 40–80 weight percent of a copolymer fraction of ethylene and propylene or another $CH_2=CHR$ alpha-olefin, where R is a 2–8 carbon alkyl radical, or combinations thereof, and, optionally, minor portions of a diene, the fraction containing less than 40 weight percent of ethylene and being soluble in xylene at ambient temperature and having an intrinsic viscosity from 1.5 to 4 dl/g; where the percent by weight of the sum of the second and third fractions with respect to the total polyolefin composition is from 50 to 90 percent and the second to third fraction weight ratio being lower than 0.4.

European Patent Application EP 0400333 A2 teaches a composition comprising first, 10–60 weight percent of a homopolymer polypropylene having an isotactic index greater than 90 or or a crystalline propylene copolymer with ethylene and/or a $CH_2=CHR$ olefin where R is a 2–8 carbon alkyl radical containing more than 85 weight percent of propylene and having an isotactic index greater than 85; second, 10–40 weight percent of a crystalline polymer fraction containing ethylene, which is insoluble in xylene at room temperature; and third, 30–60 weight percent of an amorphous ethylene-propylene copolymer containing optionally small proportions of a diene, which is soluble in xylene at room temperature and contains 40–70 weight percent of ethylene; where the composition has a flex modulus smaller than 700 MPa, tension set at 75 percent, less than 60 percent, tensile stress greater than 6 MPa and notched IZOD resilience at –20© and –40° greater than 600 J/m.

U.S. Pat. No. 5,302,454 teaches a composition comprising first, 10–60 weight percent of a homopolymer polypropylene having an isotactic index greater than 90 or of a crystalline propylene copolymer with ethylene with $CH_2=CHR$ olefin where R is a 2–6 carbon alkyl radical, or combinations thereof, containing more than 85 weight percent of propylene and having an isotactic index greater than 85; second, 10–40 weight percent of a crystalline polymer fraction containing ethylene and propylene, having an ethylene content of from 52.4 percent to about 74.6 percent and which is insoluble in xylene at room temperature; and third, 30–60 weight percent of an amorphous ethylene-propylene copolymer containing optionally small proportions of a diene, soluble in xylene at room temperature and contains 40–70 weight percent of ethylene; where the composition has a flex modulus smaller than 700 MPa, tension set at 75 percent, less than 60 percent, tensile stress greater than 6 MPa and notched IZOD resilience at –20© and –40° greater than 600 J/m.

U.S. Pat. No. 5,368,927 teaches a composition comprising first, 10–60 weight percent of a homopolymer polypropylene having an isotactic index greater than 80 or of a crystalline propylene copolymer with ethylene and/or an alpha-olefin having 4–10 carbon atoms, containing more than 85 weight percent of propylene and having an isotactic index greater than 80; second, 3–25 weight percent of an ethylene-propylene copolymer insoluble in xylene at room temperature; and third, 15–87 weight percent of a copolymer of ethylene with propylene and/or an alpha-olefin having 4–10 carbon atoms, and optionally a diene, containing 20–60 percent of ethylene, and completely soluble in xylene at ambient temperature.

Another elastic polymer suitable for the practice of this invention is known as "flexible polyolefin" or FPO from Rexene of Odessa and Dallas, Tex. which has a controlled isotacticitiy. Other olefin polymer with an appropriate atactic portion and meeting the definition of "elastic" would be suitable as well.

It is important in the practice of the invention that the outer layer be made from soft fibers. By "soft fiber" what is meant is a fiber which may be made into a web where the web has a cup crush energy of less than 1200 gm-mm and cup crush load of less than 70 grams for, for example, a 1 osy (34 gsm) web. Since a soft fabric laminate is desired, the inventors have chosen the side-by-side polyethylene-polypropylene conjugate fiber spunbond fabric as the preferred outer layer. Polyethylene is known in the art as having a soft hand when used in nonwoven fabrics while polypropylene has greater strength. A conjugate fiber of the two polymers produces a strong yet soft layer which is non-elastic. A suitable soft monocomponent or homofilament fiber may be made from a Shell Chemical polypropylene copolymer designated WRD60277. Any other soft non-elastic outer layer may be substituted for the preferred soft layer provided it may be successfully bonded to the interior elastic layer(s). Other soft fiber layers include, for example, conjugate or monocomponent fibers of various types of nylon, polyester, polyolefins like polyethylene, polypropylene and polybutylene and polyolefin copolymers and blends of copolymers and/or polyolefins.

In the practice of this invention, laminates may be made by sequentially depositing onto a moving forming belt first a spunbond fabric layer, then a meltblown fabric layer and last another spunbond layer and then bonding the laminate. It is preferred that the basis weight of the meltblown layer be between 0.1 and 2 osy (3.4 and 68 gsm) and the spunbond layers between 0.2 and 2 osy (6.8 and 68 gsm) each.

The layers may be bonded together by any method known in the art to be effective. Such methods include thermal point bonding, through-air bonding and adhesive bonding.

A number of samples of material were tested in order to determine their barrier, breathability and elastic properties. The materials are described below and the results given in Table 1. The numbers reported in Table 1 are averages of 5 readings except where noted. All samples used 0.4 osy (14 gsm) side-by-side polypropylene polyethylene conjugate spunbond fiber webs produced according to U.S. Pat. No. 5,382,400 to Pike et al. as facing materials. The polymers used to produce the facings were ESCORENE® PD-3445 polypropylene and ASPUN® 6811A polyethylene from Exxon Chemical Co. of Baytown, Tex. and Dow Chemical Co. of Midland, Mich. respectively. The facings were produced at a melt temperature of 430° F. (221° C.) and 0.7 grams per hole per minute (ghm) and bonded at 252 to 255° F. (122–124° C.).

The Mullen Burst, Drape Stiffness and hydrohead tests described above under "Test Methods" were performed and the results are given in Table 1. Note that only the Examples are considered by the inventors to be within the practice of their invention.

CONTROL 1

This material is an SMS fabric comprised of the two facing spunbond layers mentioned above and a 1 osy (34 gsm) meltblown layer made from a polymer available commercially as PF-015 from Montell Chemical of Wilmington, Del. The layers were produced separately and bonded at a bonding temperature of 280° F. (138° C.) with a nip pressure of 22 psig (1140 mm Hg) at a speed of 60 feet per minute (18.3 meters/minute). None of the layers of this material is elastic.

EXAMPLE 1

This material is an SMS fabric using the two 0.4 osy conjugate spunbond facings with a 1 osy (34 gsm) elastic meltblown layer produced from a polymer available from the Dow Chemical Co. of Midland, Mich. under the trade name ENGAGE® XU58200.02 elastic polymer. This material is a polyethylene copolymer having a density of 0.87 g/cc and a melt flow index of 30 grams/10 minutes at 190° C. and 2160 grams according to ASTM test 1238-90b. The layers were produced separately and bonded at a bonding temperature of 150° F. (65° C.) with a nip pressure of 30 psig (1550 mm Hg) at a speed of 38 feet per minute (11.6 meters/minute).

EXAMPLE 2

This material is an SMS fabric using the two 0.4 osy conjugate spunbond facings with a 1 osy (34 gsm) elastic meltblown layer produced from a polyethylene polymer designated EXACT® 4014 by the Exxon Chemical Company of Houston, Tex. The layers were produced separately and bonded at a bonding temperature of 150° F. (65° C.) with a nip pressure of 30 psig (1550 mm Hg) at a speed of 38 feet per minute (11.6 meters/minute).

EXAMPLE 3

This material is an SMS fabric using the two 0.4 osy conjugate spunbond facings with a 2 osy (68 gsm) elastic meltblown layer produced from a blend of 95 weight percent of a polymer available from the Dow Chemical Co. of Midland, Mich. under the trade name ENGAGE® XU58200.02 elastic polymer and 5 weight percent of a polymer available from the Shell Chemical Co. under the trade name Kraton® G-2755. Kraton® G-2755 is a styrene/ethylene/butadiene/styrene polymer (SEBS). The layers were produced separately and bonded at a bonding temperature of 150° F. (65° C.) with a nip pressure of 30 psig (1550 mm Hg) at a speed of 38 feet per minute (11.6 meters/minute).

TABLE 1

| Sample | Basis Weight (gsm) | Drape CD (cm) | Drape MD (cm) | Hydro-head (mbar) | Mullen Burst (psi) |
|---|---|---|---|---|---|
| Control | 1.83 | 3.1 | 5.17 | 21.3 | 26.6 |
| Example 1 | 1.7 | na | 2.08* | 14 | 22.25 |
| Example 2 | 1.82 | 2.27 | 2.5 | 14.3 | 22.3 |
| Example 3 | 2.73 | 2.42 | 2.07 | 14.3 | 22.3 |

*2 samples

The results in Table 1 show that the material of this invention has good barrier properties and burst strength while providing improved drape stiffness. In particular it should be noted that the laminates of this invention have a drape stiffness (in the MD) less than half of a similar fabric having a layer of meltblown non-elastic fibers in place of the layer of meltblown elastic fibers. Surprisingly, even the heavier basis weight Example 3 has an MD drape of less than half of the Control and all the Examples have an MD drape of at most 2.5 cm. In regard to the burst strength, it should be noted that the fabric of this invention did not "burst" in the traditional sense of a catastrophic hole being created in the fabric as was the case with the control. Instead, the fabric of this invention gave way in a more controlled, slow manner, due presumably to the elastic center layer.

The inventors believe that the highly conforming, breathable barrier material of this invention provides a mix of attributes which is different from and superior to that of current competitive materials. One would not have expected a soft laminate where the layer producing the softness and conformability of the laminate was sandwiched in the interior and surrounded by non-elastic layers. Previous attempts at producing soft laminates have taught away from this approach by focusing on the exterior layers of the laminate.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A laminate having a hydrohead of at least 10 millibars comprising at least one layer of meltblown elastic olefin polymer fibers thermally bonded on at least one side with a layer of soft fibers of a nonelastic material greater than 7 microns in average diameter.

2. The laminate of claim 1 which has a drape stiffness less than half of a similar fabric having a layer of meltblown non-elastic fibers in place of said layer of meltblown elastic fibers.

3. The fabric of claim 2 wherein said layer of soft fibers is made by the spunbond process.

4. The fabric of claim 3 wherein said soft fibers are sheath/core polypropylene/polyethylene fibers.

5. The fabric of claim 3 wherein said soft fibers are side-by-side polypropylene/polyethylene fibers.

6. The fabric of claim 1 in which said elastic fibers are made from an elastic polymer selected from the group consisting of polyolefins, polyurethanes, copolyesters, polyamide polyether block copolymers, ethylene vinyl acetates (EVA), copoly(styrene/ethylene-butylene), poly(styrene/ethylene-propylene-styrene), poly(styrene/ethylene-butylene/styrene), A-B-A-B tetrablock copolymers and blends thereof.

7. The fabric of claim 6 wherein said elastic fibers are made from elastic polyolefin.

8. The fabric of claim 6 wherein said at least one layer of elastic fibers comprise a layer of elastomeric polyolefin and a layer of another elastic.

9. The fabric of claim 1 wherein said layers are joined by a process selected from the group consisting of thermal bonding, ultrasonic bonding and adhesive bonding.

10. The fabric of claim 1 wherein said at least one elastic layer has a basis weight of between 0.1 and 2 osy.

11. The fabric of claim 1 wherein said non-elastic layers each have a basis weight between 0.2 and 2 osy.

12. An infection control product comprising the fabric of claim 1.

13. An outer cover for a personal care product comprising the fabric of claim 1.

14. A diaper comprising the outer cover of claim 13.

15. A feminine hygiene product comprising the outer cover of claim 13.

16. A laminate comprising at least one layer of meltblown elastic fibers bonded on either side with a layer of soft non-elastic fibers of greater than 7 microns in average diameter.

17. A laminate having a hydrohead of at least 10 millibars comprising at least one layer of meltblown elastic olefin polymer fibers thermally bonded on either side with a layer of soft fibers of a nonelastic material greater than 7 microns in average diameter.

18. A garment selected from the group consisting of industrial work wear and coveralls, undergarments, pants, shirts, jackets, gloves and socks and comprising the fabric of claim 17.

19. The fabric of claim 16 wherein said layers of soft fibers are made by the spunbond process.

20. The fabric of claim 16 wherein said soft fibers are sheath/core polypropylene/polyethylene fibers.

21. The fabric of claim 16 wherein said soft fibers are side-by-side polypropylene/polyethylene fibers.

22. An infection control product having a hydrohead of at least 10 millibars comprising at least one layer of elastic olefin polymer meltblown fibers thermally bonded on either side with a layer of conjugate spunbond fibers of a nonelastic material, wherein said laminate has a drape stiffness of at most 2.5 cm.

23. The infection control product of claim 22 which is a medical gown.

24. The infection control product of claim 22 which is a surgical drape.

* * * * *